(12) United States Patent
Nuijen et al.

(10) Patent No.: US 8,420,130 B1
(45) Date of Patent: Apr. 16, 2013

(54) PHARMACEUTICAL FORMULATION OF A DIDEMNIN COMPOUND

(75) Inventors: Bastiaan Nuijen, Amsterdam (NL); Jacob Hendrik Beijnen, Amsterdam (NL); Roland Elizabeth Cornelis Henrar, Amsterdam (NL); Andres Gomez, Madrid (ES); Jose Jimeno, Madrid (ES)

(73) Assignee: Pharma Mar S.A., Madrid (ES)

( * ) Notice: Subject to any disclaimer, the term of this patent is extended or adjusted under 35 U.S.C. 154(b) by 0 days.

(21) Appl. No.: 09/622,433

(22) PCT Filed: Feb. 18, 1999

(86) PCT No.: PCT/GB99/00511

§ 371 (c)(1), (2), (4) Date: May 10, 2002

(87) PCT Pub. No.: WO99/42125

PCT Pub. Date: Aug. 26, 1999

(30) Foreign Application Priority Data

Feb. 18, 1998 (GB) .................................. 9803448.1

(51) Int. Cl.
*A61K 36/00* (2006.01)
*A61K 31/47* (2006.01)

(52) U.S. Cl.
USPC .......................................... 424/725; 514/310

(58) Field of Classification Search .................... 514/310
See application file for complete search history.

(56) References Cited

U.S. PATENT DOCUMENTS

| | | | | |
|---|---|---|---|---|
| 4,342,744 | A | * | 8/1982 | Arai et al. .................. 424/70.15 |
| 4,493,796 | A | | 1/1985 | Rinehart, Jr. |
| 4,670,262 | A | | 6/1987 | Battelli et al. ................. 424/131 |
| 5,294,603 | A | | 3/1994 | Rinehart |
| 5,438,072 | A | * | 8/1995 | Bobee et al. .................. 514/449 |
| 5,462,726 | A | | 10/1995 | Lodge ........................... 514/558 |
| 5,573,781 | A | * | 11/1996 | Brown et al. .................. 424/484 |
| 5,834,586 | A | | 11/1998 | Rinehart et al. |
| 5,883,135 | A | * | 3/1999 | Gyory et al. .................. 514/724 |
| 6,030,943 | A | * | 2/2000 | Crumb et al. ..................... 514/9 |
| 6,034,058 | A | | 3/2000 | Rinehart et al. |
| 6,080,877 | A | | 6/2000 | Swindell et al. |
| 6,153,731 | A | | 11/2000 | Rinehart et al. |
| 6,156,724 | A | | 12/2000 | Rinehart et al. |
| 6,365,597 | B1 | * | 4/2002 | Pribish et al. .................. 514/284 |
| 6,509,315 | B1 | | 1/2003 | Joullié et al. |
| 6,610,699 | B2 | | 8/2003 | Cavazza et al. |
| 6,710,029 | B1 | | 3/2004 | Rinehart et al. |
| 6,890,904 | B1 | | 5/2005 | Wallner et al. |
| 7,064,105 | B2 | | 6/2006 | Joullié et al. |
| 2001/0021380 | A1 | | 9/2001 | Pluenneke |
| 2002/0098185 | A1 | | 7/2002 | Sims et al. |
| 2003/0044893 | A1 | | 3/2003 | Baum et al. |

FOREIGN PATENT DOCUMENTS

| | | |
|---|---|---|
| EP | 0 048 149 | 3/1982 |
| EP | 0 048 149 A1 | 3/1982 |
| EP | 0 393 883 | 10/1990 |
| EP | 1 054 686 | 5/2002 |
| ES | 2 102 322 | 7/1997 |
| WO | WO 91/04985 | 4/1991 |
| WO | WO 93/00362 | 1/1993 |
| WO | WO 98/01352 | 1/1998 |
| WO | WO 98/17275 | 4/1998 |
| WO | WO 98/17302 | 4/1998 |
| WO | WO 98/50048 | 11/1998 |
| WO | WO 99/42125 | 8/1999 |
| WO | WO 00/06134 | 2/2000 |
| WO | WO 00/71135 | 11/2000 |
| WO | WO 01/35974 | 5/2001 |
| WO | WO 01/76616 | 10/2001 |
| WO | WO 02/02596 | 1/2002 |
| WO | WO 02/30441 | 4/2002 |
| WO | WO 03/033013 | 4/2003 |
| WO | WO 2004/080421 A2 | 9/2004 |

OTHER PUBLICATIONS

Ady-Vago, N. et al., "L-Carnitine as a Protector Against Aplidine Induced Skeletal Muscle Toxicity", *Proceedings of the American Association for Cancer Research*, vol. 42, pp. 545 (Mar. 2001).

Bergeron, Raymond J. et al., "Antineoplastic and Antiherpetic Activity of Spermidine Catecholamide Iron Chelators", *Biochemical and Biophysical Research Communications*, vol. 121, No. 3, pp. 848-854 (1984).

Broggini, M. et al., "Aplidine Blocks VEGF Secretion and VEGF/VEGF-RI Autocrine Loop in a Human Leukemic Cell Line", *11th NCI-EORTC-AACR on New Drugs in Cancer Therapy*, Amsterdam (2000), Abstract 214.

Chapa, A.M. et al., "Influence of Intravenous L-Carnitine Administration in Sheep Preceding an Oral Urea Drench[1,2]", *Journal of Animal Science*, vol. 76, No. 11, pp. 2930-2937 (1998).

(Continued)

*Primary Examiner* — Christopher R Tate
*Assistant Examiner* — Randall Winston
(74) *Attorney, Agent, or Firm* — Kenneth H. Sonnefeld; King & Spalding

(57) ABSTRACT

A stable pharmaceutical composition of a didemnin compound, comprises firstly a lyophilized didemnin preparation including water-soluble material and secondly a reconstitution solution of mixed solvents.

25 Claims, No Drawings

OTHER PUBLICATIONS

Depenbrock, H. et al., "In vitro activity of aplidine, a new marine-derived anti-cancer compound, on freshly explanted clonogenic human tumour cells and haematopoietic precursor cells", *British Journal of Cancer*, vol. 78, No. 6, pp. 739-744 (1998)

Erba, E. et al., "Cell cycle phases perturbations induced by new natural marine compounds", *Annals of Oncology*, vol. 7, Supplement 1, #283, pp. 82 (1996).

Faircloth, G. at al., "Aplidine (APL) is a novel marine-derived depsipeptide with in vivo antitumor activity", *Proceedings of the American Association for Cancer Research*, vol. 39, #1551, pp. 227 (1998).

Faircloth, G. et al., "Dehydrodidemnin B (DDB) a new marine derived anti-cancer agent (MDA) with activity against experimental tumor models" and "Biological activity of thiocoraline. A new depsipeptide from a marine micromonospora", *Annals of Oncology*, vol. 7, Supplement 1, #111 and #112, pp. 34 (1996).

Faircloth, G. et al., "Preclinical characterization of Alplidine (APD), a new marine anticancer depsipeptice (MADEP)", *Proceedings of the American Association for Cancer Research*, vol. 38, #692, pp. 103 (1997).

Faircloth, G. at al., "Preclinical development of aplidine, a novel marine-derived agent with potent antitumor activity", *Annals of Oncology*, vol. 9, Supplement 2, #129, pp. 34 (1998).

Faircloth, G. et al., "Schedule-dependency of aplidine, a marine depsipeptide with antitumor activity", *Proceedings of the American Association for Cancer Research*, vol. 40, #2612, pp. 394-395 (1999).

Geldof, Albert A. et al., "Cytotoxicity and neurocytotoxicity of new marine anticancer agents evaluated using in vitro assays", *Cancer Chemother. Pharmacol.*, vol. 44, pp. 312-318 (1999).

Genin, Michael J. et al., "Synthesis and Crystal Structure of a Peptidomimetic Containing the (R)-4, 4-Spiro Lactam Type-II β-Turn Mimic", *Journal of Organic Chemistry*, vol. 58, No. 8, pp. 2334-2337 (1993).

Gomez-Fabre, P.M. et al., "Polamine contents of human breast cancer cells treated with the cytotoxic agents chlorpheniramine and dehydrodidemnin B", *Cancer Letters*, vol. 113, Nos. 1, 2, pp. 141-144 (1997).

Jimeno et al., "A Correlation of Selective Antitumor Activities of the Marine-Derived Compound Aplidine Using Different Models", *10th NCI-EORTC-AACR Symposium on Molecular Targets and Cancer Therapeutics*, Washington (1999), Abstract 311.

Jou, Gemma et al., "Total Synthesis of Dehydrodidemnin B. Use of Uronium and Phosphonium Salt Coupling Reagents in Peptide Synthesis in Solution", *Journal of Organic Chemistry*, vol. 62, No. 2, pp. 354-366 (1997).

Lobo, C. et al., "Effect of Dehydrodidemnin B on Human Colon Carcinoma Cell Lines", *Anticancer Research*, vol. 17, No. 1A, pp. 333-336 (1997).

Luber-Narod, J. et al., "In Vitro Safety Profile of Aplidine, A Marine Natural Product with Chemotherapeutic Potential", *Proceedings of the AACR*, vol. 42, Abstract 374, Mar. 2001.

Mastbergen, S.C. et al., "Cytotoxicity and neurocytotoxicity of aplidine, a new marine anticancer agent evaluated using in vitro assays", *Annals of Oncology*, vol. 9, Supplement 2, #131 (1998).

Montgomery, D.W. et al., "Didemnin B Alters the Specific Binding of Prolactin to Human Lymphocytes and Decreases the Circulating Level of Prolactin in Mice", *Federal Proceedings*, vol. 44, No. 3, pp. 634, #1311 (1985).

Montgomery, David W. et al., "Didemnin B: A New Immunosuppressive Cyclic Peptide with Potent Activity In Vitro and In Vivo[1]", *Transplantation*, vol. 40, No. 1, pp. 49-56 (1985).

Nuijen, B. et al., "Pharmaceutical development of anticancer agents derived from marine sources", *Anti-Cancer Drugs*, vol. 11, pp. 793-811 (2000).

Raymond, Eric et al., "Preliminary Results of a Phase I and Pharmacokinetic Study of Aplidine Given as a 24-hour Infusion Every 2 Weeks in Patients With Solid Tumors and Non Hodgkin's Lymphomas", Proceedings of the American Association for Cancer Research, vol. 41, #3886 (2000).

Rinehart, K., "Didemnin and its Biological Properties", *Escom.*, pp. 626-631 (1987).

Rinehart, Kenneth L. et al., "Biologically Active Peptides and Their Mass Spectra", *Pure and Applied Chemistry*, vol. 54, No. 12, pp. 2409-2424 (1982).

Rinehart, Kenneth L. et al., "Didemnins and Tunichlorin: Novel Natural Products from the Marine Tunicate Trididemnum Solidum[1]", *Journal of Natural Products*, vol. 51, No. 1, pp. 1-21 (1988).

Rinehart, Kenneth L. et al., "Total Synthesis of Didemnins A, B and $C^{1,2}$" *Journal of the American Chemical Society*, vol. 109, No. 22, pp. 6846-6848 (1987).

Rinehart, Kenneth L., Jr. et al., "Antiviral and antitumor compounds from tunicates[1,2]" *Federation Proceedings*, vol. 42, No. 1, pp. 87-90 (1983).

Rinehart, Kenneth L., Jr. et al., "Didemnins: Antiviral and Antitumor Depsipeptides from a Caribbean Tunicate", *Science*, vol. 212, No. 4497, pp. 933-935 (1981).

Rinehart, Kenneth L., Jr. et al., "Structure of the Didemnins, Antiviral and Cytotoxic Depsipeptides from a Caribbean Tunicate[1]", *Journal of the American Chemistry Society*, vol. 103, No. 7, pp. 1857-1859 (1981).

Sakai, Ryuichi et al., "Structure—Activity Relationships of the Didemnins[1,2]", *Journal of Medicinal Chemistry*, vol. 39, No. 14, pp. 2819-2834 (1996).

Seebach, Dieter et al., "Alkylation of Amino Acids without Loss of the Optical Activity: Preparation of α-Substituted Proline Derivatives. A Case of Self-Reproduction of Chirality[1,2]", *Journal of the American Chemical Society*, vol. 105, No. 16, pp. 5390-5398 (1983).

Urdiales, Jose L. et al., "Antiproliferative effect of dehydrodidemnin B (DDB), a depsipeptide isolated from Mediterranean tunicates", *Cancer Letters*, vol. 102, Nos. 1,2, pp. 31-37 (1996).

Vervoort, Helene et al., "Tamandarins A and B: New Cytotoxic Depsipeptides from a Brazilian Ascidian of the Family Didemnidae"; *The Journal of Organic Chemistry*, vol. 65, No. 3, pp. 782-792 (2000).

Hudes, G.R., "Phase II trial of 96-hour paclitaxel plus oral estramustine phosphate in metastatic hormone-refractory prostate cancer", *J. Clin Oncol.*, 15(9):3156-63 (1997).

Matsuoka, M., "Comparison of the effects of 1-carnitine, d-carnitine and acetyl-1-carnitine on the neurotoxicity of ammonia", *Biochemical Pharmacology*, (46(1):159-164 (1993).

Mead Johnson Oncology Products, Taxol (Paclitaxel) Injection Labeling Revision (Apr. 9, 1998).

Rinehart, K., "Antitumor compounds from tunicates", *Medicinal Research Reviews*, 20(1):1-27; Wiley Interactive Science Journal, Pub. online Dec. 22, 1999.

Virmani, M.A., "Protective actions of 1-carnitine and acetyl-1-carnitine on the neurotoxicity evoked by mitochondrial uncoupling or inhibitors", *Pharmacological Research*, 32(6):383-389 (1995).

Nuijen et al., "Pharmaceutical Development of a Parenteral Lyophilized Formulation of the Novel Antitumor Agent Aplidine", PDA Journal of Pharmaceutical Sciene & Technology, vol. 54, No. 3, May/Jun. 2000, pp. 193-208.

"Mannitol", Handbook of Pharmaceutical Excipients, Second Edition, Edited by Ainley Wade and Paul J. Weller, 1994, pp. 294-298.

Bennett, J. Claude, and Fred Plum,eds. *Cecil Textbook of Medicine*, "Part XIV—Oncology", W. B. Saunders & Company, 20th Ed., vol. 1, pp. 1004-1010 (1996).

Committee for Proprietary Medicinal Products (CPMP)—"Note for Guidance on Evaluation of Anticancer Medicinal Products in Man", *The European Agency for the Evaluation of Medicinal Products*, EMEA, London, England, CPMP/EWP/205/95 rev. 1 corr, 14 pages, (2001).

DeVita, Jr., Vincent T, Samuel Hellman, and Steven A Rosenberg, eds. *Cancer: Principles and Practice of Oncology*, "Section 3—Cancer of the Pancreas", Lippincott Williams & Wilkins, 7th Ed., 7 pages, (2005).

Draetta, Giulio et al., "Section V. Topics in Biology—Chapter 25. Cell Cycle Control and Cancer", *Annual Reports in Medicinal Chemistry*, pp. 241-248, 1996.

Geldof et al., "Cytotoxicity and Neurocytotoxicity of New Marine Anticancer Agents Evaluated Using in Vitro Assays", *Cancer Chemother. Pharmacol.*; 44 321-318, (1999).

Hansen, Richard et al., "Continuous 5-Fluorouracil (5FU) Infusion in Carcinoma of the Pancreas: A Phase II Study", *American Journal of Medical Science*, 295:91-93, (1988).

Kerbel, Robert S., "What is the Optimal Rodent Model for Anti-Tumor Drug Testing?", *Cancer and Metastasis Reviews*, 17: 301-304, (1999).

O'Neil, Maryadele J., Ann Smith and Patricia E. Heckelman, eds. *The Merck Index—An Encyclopedia of Chemicals, Drugs, and Biologicals*, Merck & Co., Inc., 13th Ed., p. 1791, (2001).

Raymond, N. Ady-Vago et al., "25th Congress of the European Society of Medicinal Oncology", Hamburg, Germany, Oct. 13-17, 2000, reported in the *Annals of Oncology*, Kluwer Academic Publishers, Supplement 4 to vol. 11, Abstract 610PD, 2 pages, (2000).

Tempero, Margaret, et al., *Clinical Practice Guidelines in Oncology—v.2.2006* —"Pancreatic Adenocarcinoma" National Comprehensive Cancer Network, http://www.neen.org/professionals/physician_gls/PDF/pancreatic.pdf, 41 pages, (2006).

Urdiales et al., "Antiproliferative Effect of Dehydrodidemnin B (DDB), a Depsipeptide Isolated from Mediterranean Tunicates", *Cancer Letters*, 102:31-37, (1996).

U.S. National Cancer Institute, U.S. National Institutes of Health, www.cancer.gov, "FactSheet", 6 pages, http://www.cancer.gov/cancertopics/factsheet/information/clinical-trials, May 19, 2006.

U.S. National Cancer Institute, U.S. National Institutes of Health, www.cancer.gov., "Pancreatic Cancer (PDQ®): Treatment", 3 pages, http://www.cancer.gov/cancertopics/pdq/treatment/pancreatic/healthprofessional, Mar. 6, 2006.

Van-Boxtel, C. J., B. Santoso and I. R. Edwards, eds. *Drug Benefits and Risks: International Textbook of Clinical Pharmacology*, "Drug Development", Chapter 9, pp. 91-102, (2001).

Chauhan, D. et al., "Multiple Myeloma Cell Adhesion-Induced Interleukin-6 Expression in Bone Marrow Stromal Cells Involves Activation of NF-κB," *Blood*, 87(3):1104-1112 (1996).

"Didemnin B," *Drugs of the Future*, 20(1):77 (1995).

Faircloth, G. et al., "Marine (MA) Depsipeptides (DEP) with Activity (A) against Solid Tumours (ST) Models," *Proceedings 8th ECCO Congress*, 31A (Suppl. 5):S29, Abstract No. 122 (1995).

Faircloth, G. et al., "Preclinical Development of Aplidine, a Novel Marine-Derived Agent with Potent Antitumor Activity," *Annals of Oncology*, 9 (Suppl. 2):34, Abstract No. 129 (1998).

Giovanella, B.C. et al., "Correlation Between Response to Chemotherapy of Human Tumors in Patients and in Nude Mice," *Cancer*, 52(7):1146-1152 (1983).

Hideshima, T. et al., "The Proteasome Inhibitor PS-341Inhibits Growth, Induces Apoptosis, and Overcomes Drug Resistance in Human Multiple Myeloma Cells," *Cancer Res.*, 61:3071-3076 (2001).

Jimeno, J. et al., "Translational Studies Supporting the Clinical Development of Aplidine (APL) in Pediatric Leukemia,"*Annals of Oncology*, 13 (Suppl. 5):19, Abstract No. 65P (2002).

Mayer, S.C. et al., "Synthesis of New Didemnin B Analogs for Investigations of Structure/Biological Activity Relationships," *J. Org. Chem.*, 59(18):5192-5205 (1994).

Mitsiades, C.S. et al., "TRAIL/Apo2L Ligand Selectively Induces Apoptosis and Overcomes Drug Resistance in Multiple Myeloma: Therapeutic Applications," *Blood*, 98(3):795-804 (2001).

Mitsiades, C.S. et al., "Activation of NF-kappaB and Upregulation of Intracellular Anti-Apoptotic Proteins via the IGF-1/Akt Signaling in Human Multiple Myeloma Cells: Therapeutic Implications," *Oncogene*, 21(37):5673-5683 (2002).

Mitsiades, N. et al., "Molecular Sequelae of Proteasome Inhibition in Human Multiple Myeloma Cells," *Proc Natl Acad Sci USA*, 99(22):14374-14379 (2002).

Mitsiades, N. et al., "The Proteasome Inhibitor PS-341 Potentiates Sensitivity of Multiple Myeloma Cells to Conventional Chemotherapeutic Agents: Therapeutic Applications," *Blood*, 101(6):2377-2380 (2003).

Mitsiades, N. et al., "Molecular Sequelae of Histone Deacetylase Inhibition in Human Malignant B Cells," *Blood*, 101(10):4055-4062 (2003).

Palangie, T. et al., "Dose-Intense Salvage Therapy After Neoadjuvant Chemotherapy: Feasibility and Preliminary Results," *Cancer Chemother. Pharmacol.*, 44 (Suppl.):S24-S25 (1999).

Uchiyama, H. et al., "Adhesion of Human Myeloma-Derived Cell Lines to Bone Marrow Stromal Cells Stimulates Interleukin-6 Secretion," *Blood*, 82(12):3712-3720 (1993).

Weiss, R. et al., "A Phase II Trial of Didemnin B in Myeloma," *Investigational New Drugs*, 12(1):41-43 (1994).

Mitsiades et al., "Pre-clinical studies in support of the clinical developments of Aplidin ® (APL) for the treatment of multiple myeloma (MM)", Blood, Nov. 16, 2003, vol. 102, No. 11, p. 74a, abstract #250.

U.S. National Cancer Institute, U.S. National Institutes of Health, www.cancer.gov, "Cancer Topics—Colon and Rectal Cancer", http://www.cancer.gov/cancertopics/types/colon-rectal, 2 pages.

U.S. National Cancer Institute, U.S. National Institutes of Health, www.cancer.gov., "Gastric Cancer (PDQ®): Treatment—General Information About Gastric Cancer", http://www.cancer.gov/cancertopics/pdq/treatment/gastric/patient, 4 pages.

* cited by examiner

PHARMACEUTICAL FORMULATION OF A DIDEMNIN COMPOUND

The present invention relates to a pharmaceutical formulation, and more particularly a pharmaceutical formulation of a didemnin compound.

THE BACKGROUND

U.S. Pat. No. 5,294,603 to Rinehart claims a pharmaceutical composition comprising a didemnin, in combination with a pharmaceutically acceptable carrier, excipient or diluent. In that patent, extensive results are given for testing for biological activity, notably assay results for cytotoxicity and antiviral activity.

THE PROBLEM

In practice, there are some difficulties in preparing pharmaceutical compositions of didemnin compounds suited for administration to patients, and there is especially a need for a stable parental pharmaceutical dosage form. More specifically, didemnin compounds such as dehydrodidemnin B, also known as aplidine, require mixing with bulking agents, such as mannitol, for optimal, stable preparation of pharmaceutical dosage forms, in particular lyophilised preparations, Certain bulking agents for this purpose, such as mannitol, require water for solubilisation, while drugs such as aplidine are poorly soluble in water. However, drug delivery to patients requires resuspending of the lyophilised materials before use.

THE INVENTION

The present invention solves the problem by providing a pharmaceutical composition of a didemnin compound, comprising firstly a lyophilised didemnin preparation including water-soluble materials and secondly a reconstitution solution of mixed solvents. The mixed solvents comprise an aqueous solvent, with the water serving to dissolve the water soluble material and the other solvent serving to dissolve the didemnin compound.

PREFERRED EMBODIMENTS

The pharmaceutical formulation of this invention is typically a stable parental pharmaceutical dosage form suited for reconstitution for administration to patients as an antitumor treatment. The invention solves the problem for drugs such as aplidine, which must be presented as lyophilised mixtures of two or more substances soluble in incompatible solvents. It preferably provides, separately bottled or otherwise contained, a premixed three component surfactant/alkanol/water mixture of solvents. In order to allow for proper resuspension of such pharmaceutical dosage forms, the separately packaged solvent mixture is provided to be added to the dry lyophilised preparations containing the drug and water soluble substances such as mannitol, before administration for treatment of disease.

Preferred didemnin compounds for the pharmaceutical compositions of this invention include didemnins and didemnin derivatives, such as dehydrodidemnins, nordidemnins, didemnin congeners and didemnin analogs. The present invention is particularly directed at didemnins with limited water solubility, including for example dehydrodidemnin B, also known as aplidine.

The antitumour agent aplidine (dehydrodidemnin B) is a natural occurring cyclic depsipeptide isolated from the Mediterranean runicate *Aplidium albicans*. Aplidine has been characterised by using several chromatographic and spectrometric techniques. Solubility testing showed that aplidine exhibits poor aqueous solubility. Moreover, the long-term stability of aplidine in solution is currently unknown.

The lyophilised didemnin preparation is preferably prepared by freeze drying a didemnin/alkanol/water mix, especially using t-butanol as the alkanol. The alkanol/water mix suitably contains 25 to 60% v/v alkanol. A bulking agent such as mannitol can also be included, though other conventional water-soluble additives may be included, known to be of utility in the preparation of such lyophilised dosage forms.

The reconstitution solution preferably comprises a surfactant/alkanol/water mix, especially using a nonionic surfactant and ethanol as the alkanol. The surfactant is suitably 10 to 25% v/v of the mix; the alkanol is suitably 10 to 25% v/v of the mix; and the water is suitably 50 to 80% v/v of the mix.

EXAMPLES

Freeze-drying was performed from a 1.0 mg/ml solution aplidine in 40% v/v t-butanol in water for injection ("WFI) containing 25 mg/ml mannitol as bulking agent. Differential scanning calorimetry studies were conducted to determine the freeze-drying cycle parameters. The prototype, containing 1.0 mg aplidine and 25 mg mannitol per vial was found to be the optimal formulation in terms of solubility, length of the freeze-during cycle and dosage requirements.

A solution composed of 15/15/70% (v/v/v) Cremophor EL/ethanol absolute/WFI was found to the optimal reconstitution solution, Cremophor EL being a glycerol-polyethylene glycol ricinoleate available from BASF in Germany.

Dilutions of reconstituted product with normal saline up to 1:200 showed it to be stable for at least 24 hours after preparation. Quality control of the freeze-dried formulation demonstrated that the manufacturing process does not change the integrity of aplidine. Shelf-life data, available thus far, show that the formulation is stable for at least 6 months when stored at +4° C. in the dark.

Thus, the preferred aplidine product of this invention is a dual-package containing:
  an injection vial containing aplidine 1 mg/vial lyophilized product, and an injection vial containing 2 ml of 15/15/70% (v/v/v) Cremophor EL/ethanol/water as reconstruction solution.

The use of 15/15/70% (v/v/v) Cremophor EL/ethanol/water as reconstitution solution for a lyophilized product is unprecedented. Thus far, the combination of Cremophor EL/ethanol in commercial available products has been used exclusively as solution vehicle (e.g., taxol or cyclosporine).

The development of the Cremophor EL/ethanol/water vehicle provides a potent co-solvent/surfactant system which can be applied as reconstitution solution in future drug formulations and allows the addition of a water soluble bulking agent such as mannitol. Furthermore, by decreasing the relative amount of Cremophor EL, a less toxic vehicle is created.

The manufacturing procedure of the lyophilized product has also a special feature. Normally, freeze-drying of a drug is performed from a drug solution in water. In the case of aplidine, a 40% (v/v) t-butanol/water mixture is preferably used as freeze-drying medium. Although previously described (e.g. rhizoxin), freeze-drying from a 40% t-butanol/water mixture is not common practice.

In conclusion, the combination of lyophilisation of a drug from a t-butanol/water mixture and the subsequent reconstitution of the lyophilized product with 15/15/70% (v/v/v) Cremophor EL/ethanol/water is unique.

The invention claimed is:

1. A kit comprising firstly a lyophilized didemnin preparation and secondly, and separately contained, a reconstitution solution of mixed solvents, wherein the lyophilized didemnin preparation comprises a didemnin compound and a water-soluble bulking agent;

wherein the reconstitution solution of mixed solvents comprises water for injection, an alkanol, and a nonionic surfactant, wherein the nonionic surfactant is 10 to 25% v/v of the solution; the alkanol is 10 to 25% of v/v of the solution; and the water for injection is 50 to 80% v/v of the solution, wherein the water for injection is present in an amount sufficient to allow solubilization of the water-soluble bulking agent, and the alkanol is present in an amount sufficient to allow solubilization of the didemnin compound in the lyophilized didemnin preparation; and wherein reconstitution of the lyophilized didemnin preparation with the reconstitution solution of mixed solvents provides a parenterally suitable preparation.

2. A kit according to claim 1, wherein the kit comprises an amount of the lyophilized didemnin preparation that is suitable for the treatment of a tumor in a patient.

3. A kit according to claim 1, wherein the didemnin compound is selected from didemnins, dehydrodidemnins, nordidemnins, didemnin congeners and didemnin analogs.

4. A kit according to claim 3, wherein the didemnin compound is aplidine.

5. A kit according to claim 1, which comprises a vial of lyophilized didemnin preparation comprising a water-soluble bulking agent, and a separate vial of a premix of nonionic surfactant/ethanol/water for injection.

6. A kit according to claim 1, which comprises a vial of the lyophilized didemnin preparation and a separate vial of the reconstitution solution of mixed solvents.

7. A kit according to claim 1, wherein the didemnin compound is a dehydrodideminin.

8. The kit of claim 1, wherein the water-soluble bulking agent is mannitol.

9. The kit of claim 1, wherein the nonionic surfactant is Cremophor EL.

10. The kit of claim 1, wherein the alkanol is ethanol.

11. The kit of claim 1, wherein the lyophilized didemnin preparation is stable for at least 6 months when stored at +4° C. in the dark.

12. The kit of claim 1, wherein the weight of the water-soluble bulking agent that is present in the lyophilized didemnin preparation is greater than the weight of the didemnin compound that is present in the lyophilized didemnin preparation.

13. The kit of claim 1, wherein the ratio of the weight of the water-soluble bulking agent that is present in the lyophilized didemnin preparation to the weight of the didemnin compound that is present in the lyophilized didemnin preparation is 25:1.

14. The kit of claim 1, wherein the reconstitution solution mixed solvents comprises cremorphor EL, ethanol, and water for injection in a ratio 15/15/70% (v/v/v).

15. A reconstituted pharmaceutical composition comprising:

a didemnin compound;
a water-soluble bulking agent;
a nonionic surfactant;
an alkanol; and
a water for injection, wherein the nonionic surfactant is 10 to 25% v/v of the nonionic surfactant/alkanol/water for injection mix; the alkanol is 10 to 25% v/v of the nonionic surfactant/alkanol/water for injection mix; and the water for injection is 50 to 80% v/v of the nonionic surfactant/alkanol/water for injection mix and wherein the water for injection is present in an amount sufficient to allow solubilization of the water-soluble bulking agent, and the alkanol is present in an amount sufficient to allow solubilization of the didemnin compound.

16. The pharmaceutical composition of claim 15, wherein the water-soluble bulking agent is mannitol.

17. The pharmaceutical composition of claim 15, wherein the didemnin compound is selected from didemnins, dehydrodidemnins, nordidemnins, didemnin congeners and didemnin analogs.

18. The pharmaceutical composition of claim 15, wherein the didemnin compound is aplidine.

19. The pharmaceutical composition of claim 15, wherein the nonionic surfactant is Cremophor EL.

20. The pharmaceutical composition of claim 15, wherein the alkanol is ethanol.

21. The pharmaceutical composition according to claim 15, wherein the didemnin compound is a dehydrodidemnin.

22. The reconstituted pharmaceutical composition of claim 15, wherein the reconstituted pharmaceutical composition is stable for at least 24 hours after dilution with normal saline up to 1:200.

23. The reconstituted pharmaceutical composition of claim 15, wherein the weight of the water-soluble bulking agent that is present in the reconstituted pharmaceutical composition is greater than the weight of the didemnin compound that is present in the reconstituted pharmaceutical composition.

24. The reconstituted pharmaceutical composition of claim 15, wherein the ratio of the water-soluble bulking agent that is present in the reconstituted pharmaceutical composition is greater than the weight of the didemnin compound that is present in the reconstituted pharmaceutical composition is 25:1.

25. The reconstituted pharmaceutical composition of claim 15, comprising a didemnin, a water-soluble bulking agent, cremophor EL, ethanol, and water for injection, wherein the cremophor EL, ethanol, and water for injection are in a ratio 15/15/70% (v/v/v).

* * * * *